United States Patent [19]

Carroll, Jr.

[11] Patent Number: 5,365,792

[45] Date of Patent: Nov. 22, 1994

[54] METHOD OF DETERMINING STRETCH CHARACTERISTICS OF THERMOPLASTIC ARTICLES

[75] Inventor: Max L. Carroll, Jr., Kingsport, Tenn.

[73] Assignee: Eastman Chemical Company, Kingsport, Tenn.

[21] Appl. No.: 964,226

[22] Filed: Oct. 21, 1992

[51] Int. Cl.$^5$ ............................................. G01N 3/18
[52] U.S. Cl. ........................................ 73/788; 73/37
[58] Field of Search .................. 73/788, 837, 37, 826; 374/49, 53

[56] References Cited

U.S. PATENT DOCUMENTS 4,090,394  5/1978  Herman et al. .................. 73/37

FOREIGN PATENT DOCUMENTS 0096887  12/1983  European Pat. Off. .

OTHER PUBLICATIONS

Bueche, F. Tensile Strength of Plastics . . . Temperature. Journal of Applied Physics. vol. 26. No. 9. Sep. '55. pp. 1133–1140.

Polymer Bulletin; No. 8; 1982; pp. 480–484. Cavrot et al. "Tensile Drawing of Poly(Ethylene-Terephthalate) Ultimate Properties".

International Journal of Engineering Science; vol. 13; No. 6; 1975; UK; pp. 563–578. Schmidt. "Biaxial Stretching of Heat-Softened Plastic Sheets Using an Inflation Technique".

Polymer Engineering and Science; vol. 21; No. 4; Mar. 1981; USA; pp. 227–232; RHI-SAUSI et al. "A Biaxial Extensiometer for Molten Plastics".

Modern Packaging; vol. 30; No. 9; May 1957; US; pp. 167–168, 250 and 252. Mannheim et al. "Testing Film Package Strengths".

Polymer Testing; vol. 9; No. 1; 1990; UK; pp. 53–70. Axtell et al. "Elongational Rheometry of Thermoplastic PET in the Rubbery Region".

Primary Examiner—Hezron E. Williams
Assistant Examiner—James M. Olsen
Attorney, Agent, or Firm—John F. Stevens; Harry J. Gwinnell

[57] ABSTRACT

Disclosed are a method and apparatus for determining the stretching characteristics of thermoplastic articles such as bottles on a consistently accurate basis by making an initial measurement such as dimension or volume, stretching the article to the onset of strain hardening, and correlating the measurements to a physical property such as inherent viscosity, intrinsic viscosity or molecular weight of the thermoplastic article.

16 Claims, 3 Drawing Sheets

METHOD OF DETERMINING STRETCH CHARACTERISTICS OF THERMOPLASTIC ARTICLES

TECHNICAL FIELD

This invention relates in general to a method of determining the stretching characteristics of thermoplastic articles having a predetermined relation of natural stretch ratio to a selected physical property. More specifically, this invention relates to a method of determining the stretching characteristics of thermoplastic articles such as bottles on a consistently accurate basis by making an initial measurement such as dimension or volume, stretching the article to the onset of strain hardening, and correlating the measurements to a physical property such as inherent viscosity, intrinsic viscosity or molecular weight of the thermoplastic article.

BACKGROUND OF THE INVENTION

While the discussion herein will be, for the most part, directed to bottles made of polyethylene terephthalate (PET) polymers and copolymers, it should be understood that the invention has wide application in thermoplastic articles of various polymers. However, a discussion of the invention as it pertains to such bottles is adequate for a full understanding thereof. Also, it is well known that inherent viscosity (IhV), as well as intrinsic viscosity, are often used in the art as an indication of molecular weight. Hence, IhV, will be used for the most part in describing the present invention herein. IhV is measured at 25° C. using 0.50 gram polymer per 100 mL of a solvent consisting of 60% by weight phenol and 40% by weight tetrachloro-ethane.

Tg (glass transition temperature) is measured using conventional DSC (differential scanning colorimetry) techniques.

When producing beverage bottles from polymers such as PET, it is important that the polymer be well oriented during stretching. Proper orientation results in uniform material distribution in most areas of the bottle. Some portions of the bottle, such as the threads, support ring, and center region of the base, are not oriented. Attaining the proper orientation is dependant upon the IhV. If the IhV is too low, the bottle will have thin sidewalls which causes a reduction in the shelf-life of the beverage, and the bottle will also expand excessively due to internal pressure.

It should be noted that while the stretching characteristics of PET are highly dependant upon IhV, other factors also have an effect, e.g., the PET's temperature when stretching occurs, the PET's level of copolymerization, moisture content, amount of free volume relaxation, and rate of stretching have an effect oil the amount that PET will stretch. However, if these variables are constant for all tests, comparative results are achieved.

Bottles are generally made by first injection molding a preform, which is then blown into a bottle. It is not practical for PET bottle producers to check bottle preform IhV in their plants. IhV measurements are expensive and can be rather erratic unless the test is very carefully controlled. Therefore, IhV testing is not common in the bottle industry. As a result, most bottle producers often do not learn of IhV problems until bottles are blown (typically 1 to 14 days after molding).

It has now been discovered that IhV can be determined on a relative basis by relating it to the natural stretch ratio (NSR) of articles to be tested. That is, if the NSR of thermoplastic bottles is always determined under the same conditions for different samples, the NSR will indicate the IhV (or intrinsic viscosity or molecular weight). In this way, for example, if an IhV of 0.72 is desired, the NSR of that article can be determined under given conditions (control). A graph for NSR plotted against IhV can be developed. Thermoplastic articles can then be stretched, either unilaterally or bilaterally, under the same conditions as the "control". If this ratio is the same as for the control, it will indicate the same IhV. Or, if this ratio is different, the IhV can be determined by referring to the graph.

It is believed that the present invention may be used by bottle producers to free-blow bottles and then plot bottle volume on statistical process control charts as an indication of IhV.

Free-blowing of PET preforms is a well known technique used to obtain empirical data on the stretching characteristics of a particular PET formulation. Such data are used to design a preform for that formulation which will yield the desired bottle properties. Free-blow involves heating the bottle preform to a temperature above its Tg and then blowing it without a mold such that it is free to expand without restriction until the onset of strain hardening is reached. In PET articles, it will be apparent that the onset of strain hardening has been reached when pearlescence (caused by microcracks) appear. Thus, the free-blow conditions (heating time and blow pressure) are adjusted so that the free-blown bottle will exhibit a slight amount of pearlescence.

Once a particular design is put into commercial use, it is important that the preform IhV be maintained at a target design IhV, or a reasonable variation thereof. If the preform IhV is not near the target IhV, problems will occur during the bottle blowing process. Typically, IhV variations of plus or minus 0.03 dl/g can be tolerated.

A basic problem has existed in the past in consistently heating preforms to the same temperature during each free-blow test to consistently obtain accurate results.

BASIC DESCRIPTION OF THE DRAWINGS

DESCRIPTION OF THE INVENTION

Figure 1:
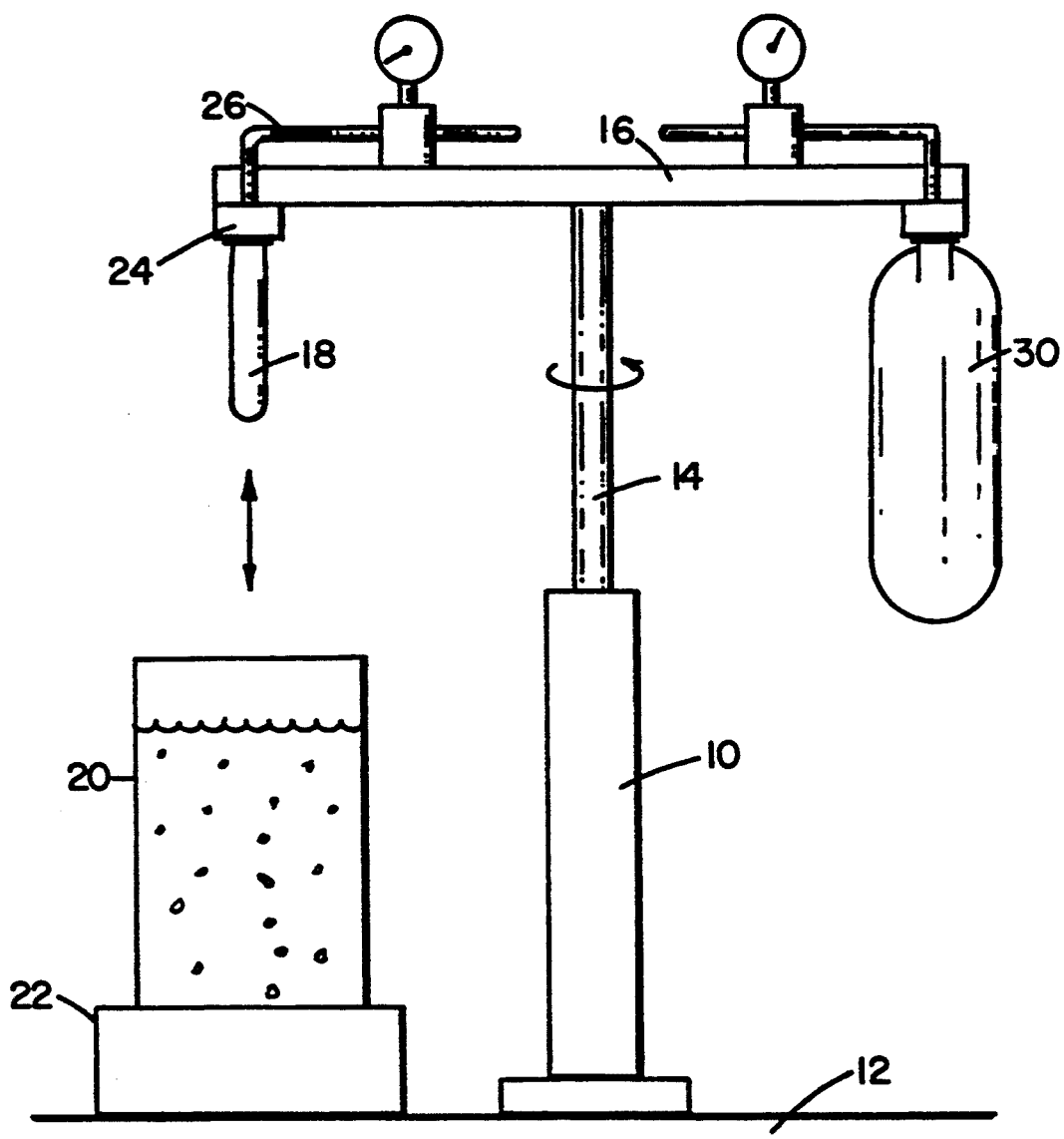
FIG. 1 is an elevation view of apparatus suitable for carrying out the present invention.

In general, the present invention provides a method of analyzing samples of thermoplastic articles for a selected physical property in a manner such that consistent results are obtained which comprises a) heating the articles by at least partially submerging them in a boiling liquid until at least the glass transition temperature is reached over the submerged portion, b) stretching the articles at a temperature of at least their glass transition temperature until the onset of strain hardening (OSH) occurs, and c) determining a desired property which is, or is related to, the elongation of said articles.

As a practical application, this invention provides a convenient method for insuring consistency of wall thicknesses of thermoplastic bottles, which is of course necessary for quality control reasons. For example, if a bottle is blown from a preform having the correct molecular weight, that bottle can be used as a control for others by determining its volume after free-blowing. All other samples having the correct molecular weight polymer should in turn have the same volume after free-blowing. For comparable results, however, the temperature at blowing must be consistently the same for all samples. It is difficult to insure the same temperature using conventional heating methods. Applicant has found that these temperatures can be held consistently the same if the heat is supplied from boiling liquid, preferably water. Natural stretch ratios at that temperature (at, or above, the Tg of the polymer) can be compared. Rather than measure NSR, however, it may be preferable to make some other measurement such as volume of bottles blown to the onset of strain hardening, which can be correlated to NSR by a simple mathematical relation.

The present invention also provides an apparatus for analyzing samples of thermoplastic articles for a selected physical property in a manner such that consistent results are obtained which comprises a) means for at least partially submerging the articles in a boiling liquid, b) means for withdrawing the articles from the boiling liquid after they have been heated to at least their glass transition temperature, c) means for stretching the thermoplastic articles at a temperature of at least their glass transition temperature until the onset of strain hardening occurs, and d) means for determining a desired property which is, or is related to, the expansion of the articles.

More particularly, apparatus is provided for analyzing samples of thermoplastic bottle preforms of the same predetermined volume to determine the amount of expansion at the onset of strain hardening in a manner such that comparable results are obtained on a consistent basis which comprises a) a vessel for containing a liquid, b) means for supplying heat to maintain the temperature of the liquid at its boiling point for the duration of analysis, c) a movable member having means adapted to hold a bottle preform by its neck, the moveable member having a first position for holding at least a portion of said bottle preform submerged in the boiling liquid, and a second position for holding the bottle preform in a position outside said boiling liquid, d) means for expanding the bottle preforms until they reach tile onset of strain hardening, and e) means for determining the volumes of the expanded preforms for comparing with the volume of a control sample.

According to the invention there is also provided a method of determining the stretching characteristics of thermoplastic articles having a predetermined relation of natural stretch ratio to a selected physical property on a consistent basis which comprises the steps of a) determining at least one initial dimension of a sample of the article at a selected temperature (since the initial volume of preforms for a particular test is constant, obtaining the NSR is unnecessary), b) submerging the sample in a boiling liquid having a consistent boiling point, the boiling temperature of which is sufficient to heat the sample at least to its glass transition temperature, for a time sufficient for the article to reach its glass transition temperature across its thickness but without attaining appreciable crystallization, c) stretching the article in at least said initial dimension to the onset of strain hardening, d) determining the stretched dimension of the article, e) determining the ratio of the stretched dimension to the initial dimension, and f) correlating the ratio determined in e) to a precalculated association with a selected physical property.

Also, according to this invention, there is provided a method of determining the stretching characteristics of a thermoplastic container having a predetermined relation of natural stretch ratio to a selected physical property on a consistent basis which comprises the steps of a) determining the initial volume of the container at a selected temperature, b) submerging the container in a boiling liquid having a consistent boiling point, the boiling temperature of which is sufficient to heat the container to at least its glass transition temperature for a sufficient time for the container to reach its glass transition temperature across its wall thickness but without attaining appreciable crystallization, c) injecting a gas into said container to pressurize it and blow it to the onset of strain hardening, d) determining the volume of said container after step c), e) determining the ratio of the volume determined in d) with its initial volume, and f) correlating the ratio determined in step e) to a precalculated relationship with a selected physical property.

Further, according to this invention there is provided a method of determining the stretching characteristics of a thermoplastic polyester preform from which a bottle is to be blown, the polyester preform having a predetermined relation of natural stretch ratio to inherent viscosity, which comprises the steps of a) determining the initial volume of a selected major portion of the preform at a selected temperature, b) submerging the selected major portion of said preform in a boiling liquid having a consistent boiling point, the boiling temperature of which is sufficient to heat said preform to at least its glass transition temperature for a time long enough for the selected major portion to reach its glass transition temperature across its wall thickness but without attaining appreciable crystallization, c) injecting a gas into said preform under sufficient pressure to blow it to the onset of strain hardening, d) determining the volume of the blown preform after step c), e) determining the ratio of the volume determined in d) with its initial volume, and f) correlating the ratio determined in step e) to a precalculated relationship with inherent viscosity.

In the case of biaxial orientation of stretch blown thermoplastic bottles, the NSR is defined as $A2/A1$, where:

$A2$ = area of stretched surface at onset of strain hardening $A1$ = area of original (unstretched) surface In the case of uniaxial orientation, e.g., thermoplastic fiber and filament, the NSR is defined as $L2/L1$, where:

$L2$ = length of stretched segment at the onset of strain hardening $L1$ = length of original (unstretched) segment Thus, in accordance with the present invention, a boiling liquid, preferably water, is used to consistently heat the preforms to the same temperature for each test. Although a variety of other liquids may be used, boiling water is preferred for a number of obvious reasons. It is essential that the free-blow testing be done using the same conditions (e.g., temperature, blow pressure, and rate of stretching) on a day-to-day basis. Since the preform temperature has a large effect on the bottle volume, it is important that the method of heating be very consistent, and using boiling water offers that assurance. "Consistent boiling point" means that the liquid boils at a predetermined temperature consistently while at the same barometric pressure.

The temperature at which water boils is dependant upon altitude, barometric pressure, and water purity. However, the altitude will be constant for a given location and the purity of the water should be relatively consistent. It is preferred that either distilled or demineralized water be used. Variations in temperature due to changes in the barometric pressure will typically be very slight.

While water is preferred, other liquids or mixtures of liquids such as some hydrocarbons, alcohols, ketones, and esters could also be used, e.g., 2-butanol, isobutyl alcohol, n-propyl alcohol, diethyl ketone, methyl propyl ketone, methyl isobutyl ketone, n-heptane, methyl cyclohexane, and propyl acetate.

If a liquid other than water is used, the liquid should boil at a temperature of at least the Tg to soften the preform enough for it to be free-blown. The glass transition temperature of PET is about 80° C. However, the combination of temperature and heat transfer coefficient should be such that the inside surface of the preform would reach Tg prior to the outside surface crystallizing, if the preform is heated from the outside with the liquid. Obviously, heating may be done from the inside by filling the preform with the liquid, or by a combination of inside/outside heating.

In a broad sense, the present invention may be used in connection with articles such as sheet material, film and fibers as well as bottles. In such cases the film or sheet material may be unilaterally or bilaterally stretched, and fibers may be unilaterally stretched for determining natural stretch ratio. The Tg of the thermoplastic article should be attained across the thickness thereof. In the case of a preform, the Tg must be reached across the wall thickness. However, the heating should be at a temperature and time such that no appreciable crystallization occurs.

In the case of preforms, stretching is conveniently done by pressurizing and blowing the bottle until the onset of strain hardening. An inert gas, preferably air, is used for the pressurization. Other suitable inert gases will be apparent to those skilled in the art. In the case of fibers, films and sheeting, stretching may be accomplished by means known to those skilled in the art. For example, pairs of driven nip rolls, operated at selected different speeds may be used. In the case of fibers, films and sheeting, dimensions may be measured initially, i.e., before heating while the article is at a selected temperature in the solid state, and then measured at the onset of strain hardening. The difference in these measurements can be calculated readily.

In bottles, a convenient way of relating these measurements is by volume. It will be apparent to those skilled in the art that the same physical property is being measured, i.e., amount of strain until the onset of strain hardening.

Figure 2:
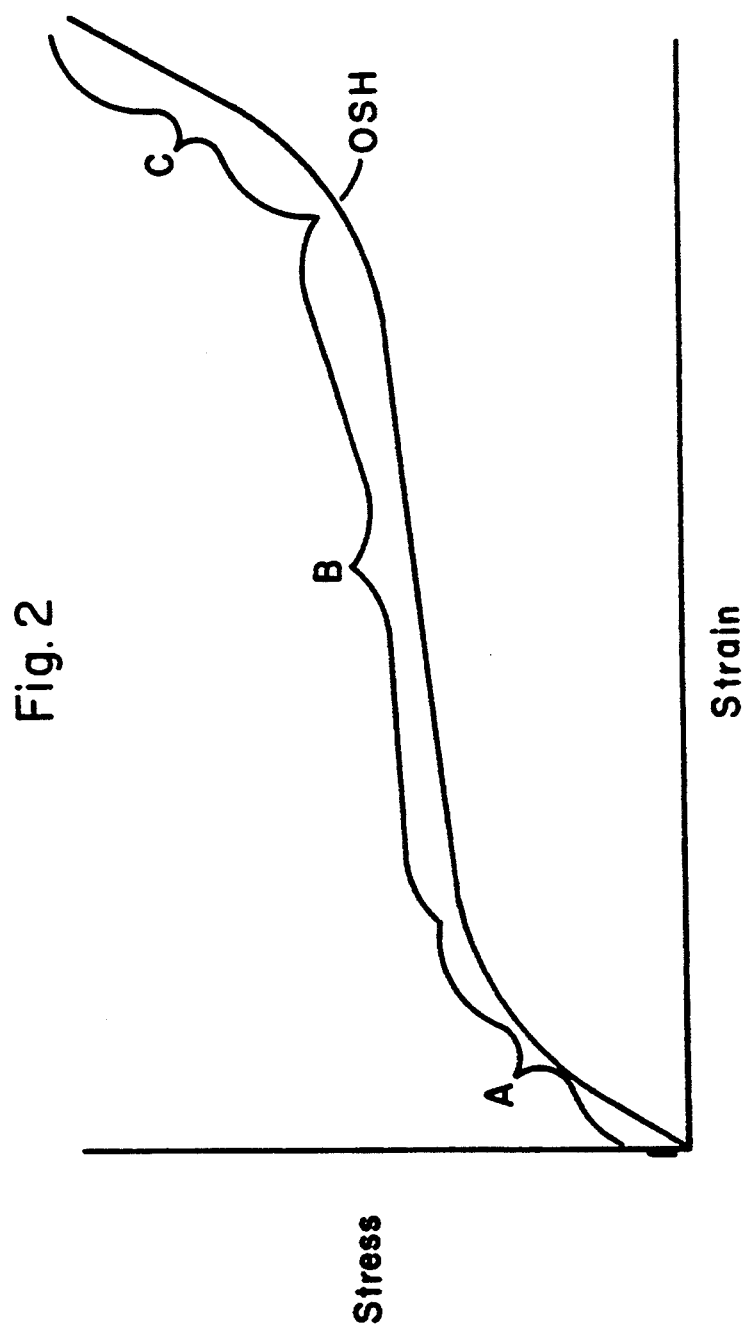
FIG. 2 is a graph showing a typical stress-strain curve for thermoplastic articles.

Referring first to FIG. 2, a stress-strain curve is illustrated which is typical of PET at a temperature of about 100° C.

In Region A, the stress rises rapidly and results in a certain amount of strain. The curve then flattens out in Region B, where the stress remains relatively constant while a large amount of strain occurs. Next the curve turns upward into Region C, the strain hardening region where strain induced crystallization takes place and the highest tensile properties are achieved. The onset of strain hardening is the transition region between Regions B and C. The onset of strain hardening may be determined as follows: Extend lines from Regions B and C until they intersect. Bisect the angle adjacent to the stress-strain curve, and extend that bisecting line to intersect the curve. The point at which that line and the curve intersect is the onset of strain-hardening.

Apparatus suitable for carrying out the present invention is illustrated in FIG. 1, which is a schematic elevation view of such apparatus. Referring to the drawings, double acting air cylinder 10 is rigidly mounted on base 12. Arm 14 of air cylinder 10 is adapted to be extended, as shown, or withdrawn, in which case bracket 16 would submerge preform 18 in the container of boiling liquid 20. The water is heated by a heater 22, which may suitably be a hot plate. Preform 18 is provided with threads during an injection molding process, as is well known to those skilled in the art, and the threads allow it to be screwed into preform holder 24. Preform holder 24 has associated therewith an air source through line 26.

In operation, the liquid is heated to its boiling point. Air cylinder 10 is actuated, placing the preform 18 in the boiling liquid. Preform 18 is maintained in this position until heated sufficiently as described herein. At that point, the air cylinder 10 extends arm 14 to carry the preform out of the boiling liquid. The hot preform 18 is rotated away from the boiling liquid, then blown to the onset of strain hardening and allowed to cool while still under pressure. The pressure is relieved and the blown bottle 30 is removed for selected measurements (e.g., volume).

It was found that bottles could be free-blown to the NSR using various combinations of heating time and blow pressure (3 to 5 minutes and 50 to 90 psi). As expected, the NSRs, and thus bottle volumes, were significantly different. However, for a particular combination of time and pressure, the resulting NSRs and volumes were generally consistent.

From the standpoint of conditions on heating time and pressure, the following points should be considered:
1. The length of time a preform needs to remain in the boiling liquid will depend primarily on its thickness.
2. The length of time must be sufficient for the inside surface of the preform to reach the glass transition temperature of the material.
3. Leaving the preform in the liquid long enough for the inside surface to reach a temperature significantly greater than 95° C. for PET will only increase the cycle time. Preferably, the inside surface is 85° to 95° C. for PET.
4. Leaving the preform in the liquid too long can result in its outer surface starting to crystallize which will effect the NSR.

5. The blow pressure needed will depend on preform thickness and on preform temperature.
6. The pressure should be sufficient to fully orient all of the material below the support ring.
7. The pressure should not induce enough stress to cause the bottle to burst.
8. Ideally, the pressure should be such that a very slight amount of "pearlescence" occurs. Pearlescence is a term commonly used in the PET bottle industry to describe a phenomenon that occurs when the onset of strain hardening is exceeded by about 5%. When that happens, microfractures occur, giving a hazy appearance with the sheen of an oyster pearl. Therefore, "pearlescence" is an excellent visual indication that the onset of strain hardening has been reached.

As an example, 200 grams of water were added to 250 pounds of PET (0.76 IhV copolymer) and blended. Three days later, the pellets were dried at 4 different sets of conditions, molded into 55-gram preforms, and then free-blown using the following conditions. Preforms from the same cavity of the injection mold were used.

1. With the water at boil, weigh the beaker of water and adjust it to insure that the water level is at a predetermined level.
2. With the preform screwed into the holder, lower it into the boiling water.
3. After 4 minutes, raise the preform and pivot it away from the beaker of boiling water.
4. Quickly wipe the preform dry. Drops of water on the preform will act as a heat sink, and thus cool those areas, which in turn prevents them from stretching properly.
5. Twenty seconds after removal from the water, pressurize the preform with 80 psig air. The inside diameter of the air line was about 0.18 inch. That diameter has an effect on the rate at which the preform is inflated, and thus the rate at which the PET stretches. The ultimate size of the free-blown bottle is somewhat dependant upon the stretch rate, with faster rates yielding smaller bottles.
6. Remove the bottle from the holder, and fill it completely with tap water, and cap it, insuring there are no air bubbles present.
7. Weigh the filled bottle, subtract the weight of the bottle and cap and record the net weight.

Figure 3:
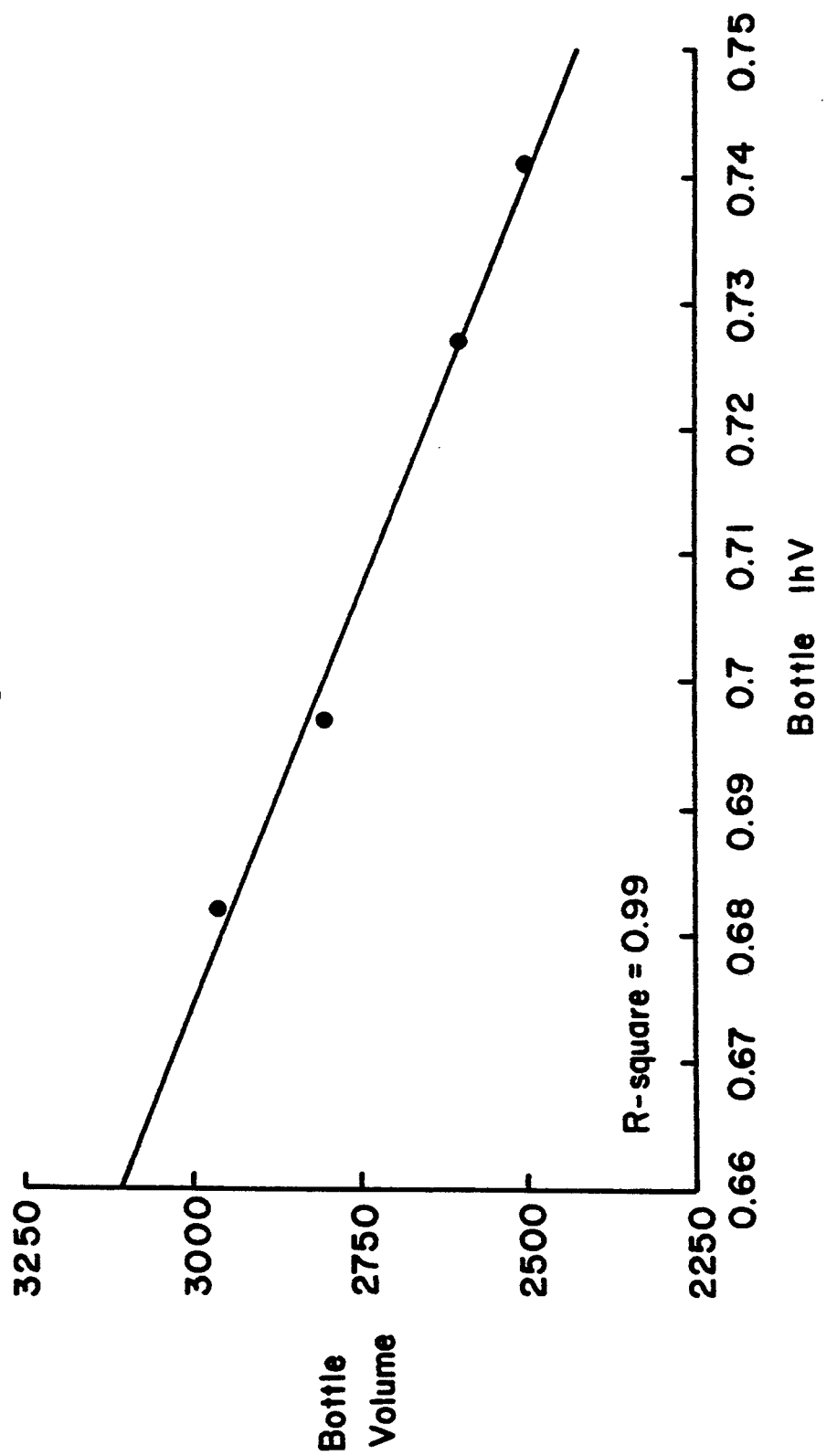
FIG. 3 is a graph illustrating bottle volume vs. bottle IhV.

Six bottles were selected and cut for IhV testing (Table 2). A graph of Average Bottle Volume Vs. Average Bottle IhV is given in FIG. 3. Furthermore, a 0.01 dl/g difference in IhV corresponds to a 75 cc difference in the free-blown bottle volume, showing that the test is sensitive enough to detect relatively small differences in IhV.

TABLE 1

| Free-Blown Bottle Volumes (Cubic Centimeter) | | | |
|---|---|---|---|
| Drying | | | |
| 250° F. for 4 Hr | 250° F. for 5 Hr | 275° F. for 6 Hr | 300° F. for 6 Hr |
| 2915 | 2715 | 2595 | 2467 |
| 2841 | 2860 | 2552 | 2500 |
| 2855 | 2784 | 2531 | 2532 |
| 2952 | 2725 | 2614 | 2485 |
| 2874 | 2814 | 2672 | 2467 |
| 3078 | 2789 | 2550 | 2444 |
| 2956 | 2837 | 2539 | 2485 |
| 2834 | 2701 | 2565 | 2490 |
| 2959 | 2727 | 2633 | 2416 |
| 2842 | 2852 | 2611 | 2524 |
| 2973 | 2815 | 2630 | 2475 |
| 3010 | 2767 | 2635 | 2522 |
| 2970 | 2791 | 2567 | 2489 |
| 2944 | 2810 | 2585 | 2525 |
| 2948 | 2761 | 2654 | 2478 |
| 3068 | 2728 | 2601 | 2546 |
| 3017 | 2913 | 2648 | 2464 |
| 3082 | 2818 | 2593 | 2506 |
| 2987 | 2883 | 2610 | 2480 |
| 3044 | 2910 | 2588 | 2531 |
| — | — | — | 2537 |
| 2957 | 2800 | 2599 | 2490 |
| | | | 2504 |
| | | | 2546 |
| | | | 2548 |
| | | | 2440 |
| | | | 2443 |
| | | | 2586 |
| | | | 2541 |
| | | | 2562 |
| | | | — |
| | | | 2501 |

TABLE 2

| Bottle IhV Data (With Corresponding Volumes) | | | | | | | |
|---|---|---|---|---|---|---|---|
| IhV | Vol. | IhV | Vol. | IhV | Vol. | IhV | Vol. |
| 0.682 | 2915 | 0.691 | 2860 | 0.727 | 2595 | 0.734 | 2500 |
| 0.666 | 3078 | 0.699 | 2725 | 0.724 | 2531 | 0.733 | 2532 |
| 0.689 | 2834 | 0.693 | 2789 | 0.730 | 2614 | 0.746 | 2444 |
| 0.693 | 2973 | 0.698 | 2701 | 0.726 | 2672 | 0.743 | 2490 |
| 0.682 | 2970 | 0.705 | 2767 | 0.731 | 2539 | 0.744 | 2416 |
| 0.677 | 2948 | 0.698 | 2810 | 0.725 | 2565 | 0.743 | 2546 |

Note: IhV data are in dl/g and volumes in cc.

The invention has been described in detail with particular reference to preferred embodiments thereof, but it will be understood that variations and modifications can be effected within the spirit and scope of the invention.

I claim:

1. The method of determining the stretching characteristics of thermoplastic articles having a predetermined relation of natural stretch ratio to a selected physical property on a consistent basis which comprises the steps of
    a) determining at least one initial dimension of a sample of said article at a selected temperature,
    b) submerging said sample in a boiling liquid, the boiling temperature of which is sufficient to heat said sample at least to its glass transition temperature, for a time sufficient for said article to reach its glass transition temperature across its thickness but without attaining appreciable crystallization,
    c) stretching said article in at least one direction to its onset of strain hardening,
    d) determining the stretched dimension of said article,
    e) determining the ratio of the stretched dimension to the initial dimension, and
    f) correlating the ratio determined in e) to a precalculated association with a selected physical property.

2. The method of claim 1 wherein said thermoplastic article in a bottle preform.

3. The method of claim 1 wherein said thermoplastic article is a polyester bottle preform.

4. The method of claim 1 wherein said selected physical property is inherent viscosity, intrinsic viscosity, or molecular weight.

5. The method of claim 1 wherein said liquid is water.

6. The method of claim 1 wherein said polyester comprises repeat units of terephthalic acid, ethylene glycol and a monomer selected from isophthalic acid or 1,4-cyclohexanedimethanol.

7. The method of claim 1 wherein the temperature of said boiling liquid is at least 80° C.

8. The method of claim 1 wherein said sample is heated to a temperature of about 80° C.-100°C. across the thickness thereof.

9. The method of determining the stretching characteristics of a thermoplastic container having a predetermined relation of natural stretch ratio to a selected physical property on a consistent basis which comprises the steps of
  a) determining the initial volume of said container at a selected temperature,
  b) submerging said container in a boiling liquid, the boiling temperature of which is sufficient to heat said container to at least its glass transition temperature for a time long enough for said container to reach its glass transition temperature across its wall thickness but without attaining appreciable crystallization,
  c) injecting a gas into said container to pressurize it and blow it to its onset of strain hardening,
  d) determining the volume of said container at its onset of strain hardening,
  e) determining the ratio of the volume determined in d) with its initial volume, and
  f) correlating the ratio determined in step e) to a precalculated relationship with a selected physical property.

10. The method of determining stretch characteristics of a thermoplastic polyester preform from which a bottle is to be blown, said polyester preform having a predetermined relation of natural stretch ratio to inherent viscosity, which comprise the steps of
  a) determining the initial volume of a selected major portion of said preform at a selected temperature,
  b) submerging said selected major portion of said preform in a boiling liquid, the boiling temperature of which is sufficient to heat said preform to at least its glass transition temperature for a time long enough for said selected major portion to reach its glass transition temperature across its wall thickness but without attaining appreciable crystallization,
  c) injecting a gas into said preform under sufficient pressure to blow it to its onset of strain hardening,
  d) determining the volume of the bottle at its onset of strain hardening,
  e) determining the ratio of the volume determined in d) with its initial volume, and
  f) correlating the ratio determined in step e) to a precalculated relationship with inherent viscosity.

11. The method of claim 10 wherein said selected physical property is inherent viscosity, intrinsic viscosity, or molecular weight.

12. The method of claim 10 wherein said liquid is water.

13. The method of claim 10 wherein said polyester comprises repeat units of terephthalic acid, ethylene glycol and a monomer selected from isophthalic acid or 1,4-cyclohexanedimethanol.

14. The method of claim 10 wherein the temperature of said boiling liquid is at least 80° C.

15. The method of claim 10 wherein said preform is heated to a temperature of about 80° C.-95° C. across the thickness thereof.

16. The method of analyzing samples of thermoplastic articles for a selected physical property in a manner such that consistent results are obtained which comprises
  a) heating said articles by at least partially submerging them in a boiling liquid until at least the glass transition temperature is reached over the submerged portion,
  b) stretching said articles at a temperature of at least their glass transition temperature until the onset of strain hardening is reached, and
  c) determining a desired property which is, or is related to, the elongation of said articles.

* * * * *